US00PP07977P

United States Patent [19]

Eubanks

[11] Patent Number: Plant 7,977

[45] Date of Patent: Sep. 15, 1992

[54] CORN PLANT NAMED TRIPSACORN

[76] Inventor: Mary W. Eubanks, 4110 Hulon Dr., Durham, N.C. 27705

[21] Appl. No.: 613,269

[22] Filed: Nov. 13, 1990

[51] Int. Cl.[5] ..... A01H 5/00
[52] U.S. Cl. ..... Plt./100
[58] Field of Search ..... Plt./89

[56] References Cited

U.S. PATENT DOCUMENTS

P.P. 6,906 7/1989 Eubanks ..... Plt. 89

OTHER PUBLICATIONS

Mangelsdorf, P. C. "*Corn Its Origin Evolution and Improvement*", 1974 The Belknap Press of Howard University Press, Cambridge, Mass. pp. 58–70.

Pasupaleti, G. V. et al. (1986) "The Cytology of the Trigernomic Hybrid" *Maize Genetics Cooperation Newsletter* 60 p. 133.

Kindiger, B., et al., (1990) "Cytological Evidence Supporting a Procedure for Directing and Enhancing Pairing Between Maize and Tripsacum" *Genome* vol. 33, pp. 495–500.

Branson, T. F., et al, (1972) "Potential for Utilizing Resistance from Relatives of Cultivated Crops" *Proceed. North Central Branch*-ESA vol. 27, pp. 91–94.

Farquharson, L. I. (1957), "Hybridization of Tripsacum and Zea" *Journal of Heredity*, vol. 40, pp. 295–299.

Galinat, W. C., "Chapter 1 The Origin of Corn" *Corn and Corn Improvement* #18 Agronomy, Am. Soc. of Agron. 1977, pp. 1–47.

Poehlman, J. M., "18 Breeding Corn (Maize)" *Breeding Field Crops*, 3rd Ed. AVI Pub. Co., Inc., 1987, pp. 451–453.

MacNeish, R. S., "The Origin of New World Civilization" *Plant Agriculture* with Freeman and Co., 1984 pp. 13–21.

*Primary Examiner*—James R. Feyrer

[57] ABSTRACT

A new and distinct corn plant that is the product of a cross between *Tripsacum dactyloides* and *Zea diploperennis*, a diploid perennial teosinte. This plant is fertile, has been proven to be cross compatible with *Zea mays* L. and offers an avenue to expand the gene pool for commercial corn varieties. The instant plant is perennial, offers outstanding drought and heat tolerance, has survived temperatures of 0 degrees Fahrenheit, and offers enhanced pest resistance for importation into corn through improvement breeding programs.

5 Drawing Sheets

BACKGROUND OF THE NEW PLANT

Two wild grasses, *Zea diploperennis* and *Tripsacum dactyloides* have been crossed to produce a novel hybrid that may improve corn by imparting beneficial characteristics including pest resistance and drought tolerance. *Zea diploperennis* (hereafter referred to as diploperennis), a diploid perennial teosinte and previously unknown wild relative of maize, was discovered on the verge of extinction in the mountains of Jalisco, Mexico in 1979. Diploperennis is in the same genus as maize, has the same chromosome number (n=10), and hybridizes easily with it. Tripsacum, a more distant relative of corn with a different chromosome number (n=18), has been crossed with maize by artificial means but has not been known to cross with teosinte. Many investigators believe that Tripsacum played a prominent role in the origin and evolution of maize, and that it has significant potential for improving corn by expanding its genetic diversity.

In 1984, crosses were made to diploperennis using Tripsacum pollen and U.S. Plant Pat. No. 6,906, was issued Jul. 4, 1989 on the hybrid from that cross. In Apr., 1985, the reciprocal cross to Tripsacum was made using diploperennis pollen. The plant germinated from the hybrid seed [labeled (Trip X 3-3)] developed normally, was fully fertile and produces viable fruits. This plant is referred to as Tripsacorn. The chromosome number determined from root tip counts is 2n=20 or 2n=18. There is evidence in late prophase and metaphase for chromosome fusion. Some chromosomes are linked end to end in a chain formation and others have the trisomic y-shaped configuration. Although the chromosome number is unexpected, it has been reasonably ascertained that the genotype for this plant is normal and stable.

Perennial plants have been propagated by means of cuttings and rhizome divisions. In field tests, they have produced new growth following winter temperatures of 0° F. and have survived summer drought for six weeks.

In preliminary field trials of backcrosses to a commercial corn line, drought tolerance and enhanced pest resistance were observed in the $F_1$ generation. Germination of seed from these crosses was 100%. The plants were fully fertile and there was no loss in productivity. Tripsacorn evidently provides a natural bridge for introducing Tripsacum germ plasm into corn, thereby establishing a link between these wild grasses and modern corn that may be beneficial in corn improvement breeding programs. The results of crossing Tripsacorn, labeled (Trip X 3-3), to corn were distinctly different from the results of crossing the patented plant Sun Dance, labeled (3-7X Trip), to corn. When Sun Dance was crossed to corn, the $F_1$ plants were depauperate in growth and highly susceptible to insects and disease; whereas plants grown from Tripsacorn X corn were sturdy, more tolerant of the drought conditions during the summer of 1988, were resistant to the plant pests that plagued the corn that season, were stocky with strong stalks and more extensive root systems, were fertile and produced ears weights equal to the corn controls.

Unique propagation of Tripsacorn through successive generations by means of cuttings has demonstrated that the new plant has not only retained the continuous and abundant production capability, but also that its distinguishing characteristics hold true from generation to generation and appear to be firmly fixed. Propagation has taken place in Tennessee, North Carolina, and Mississippi.

DESCRIPTION OF ILLUSTRATIONS

This new corn plant is illustrated by the accompanying photographs, which show:

(1) a plant grown outdoors showing the characteristic habit of many culms growing from the base, each of which produce a separate tassel at the apex;
(2) the long, narrow leaf with distinctive white midrib;
(3) an individual culm showing distinctive red coloration and ears emerging from leaf sheaths at the nodes;
(4) a close-up of a three-branched tassel with emerged anthers shedding pollen;
(5) a close-up of the two variations of single-rowed female spikes that are produced, one in which the male flowers are subtended by the female inflorescence and one that is solely a single-rowed female spike;
(6) a side view of a segment of the alternate type of inflorescence that forms a four-rowed cob consisting of paired kernels partially enclosed by hard glumes;
(7) two other side views of the cob showing the distinctive interspacing between segments with a separate section of the rachis segment showing the ball and socket abscission characteristic of the Tripsacum parent, cupule, and a removed kernel;
(8) an autoradiograph showing the banding patterns of Tripsacorn (Trp X 3-3), Sun Dance (3-7 Trip), a diploperennis parent (3-7), the Tripsacum parent (Trip) and two corn controls (CM37 and T232), when the DNA was digested by BamH1 and probed with BNL 17.07, a nuclear probe to the long arm of maize chromosome 10;
(9) an autoradiograph of DNA from the same plants digested with Bam H1 and Hind III that reveals cytoplasmic differences as evidenced by the different banding patterns of (Trip x 3-3) and (3-7 X Trip) when probed with a maize mitochondrial ATPase gene.

THE PLANT

Origin: Seedling.

Parentage:

*Seed parent.—Tripsacum dactyloides.* Source: Plant established at Indiana University, Bloomington, Ind., originally collected from Santa Claus, Spencer County, Ind., 1949–54.

*Pollen parent.—Zea diploperennis.* Source: Upper las Joyas, Sierra de Manantlan, Jalisco, Mexico, Iltis, Nee & Guzman Acc. #1250, Jan. 1979.

Classification:

*Botanic.—Zea indiana* (proposed).

Habit: Essentially erect; as many as 35 primary culms, usual number about 15.

Duration:

*Perennial.*—Sends out shoots from rhizomes. Plant will freeze at winter temperatures below 28° F., but new growth is produced in spring after winter temperatures of 0° F.

Culm:

*Height.*—Up to two meters; slender, simple with occasional branching from the nodes of the culm; glabrous; oval in cross section; diameter 1–12 cm.

*Nodes.*—Glabrous, aerial roots develop at nodes along entire culm.

*Sheath.*—Tightly closed enwrapping the culm, margins not united; glabrous; turns rose red (Pantone #18-1852) when exposed to sun, otherwise green; rose red (Pantone #18-1852, ciliate auricles at summit margins.

*Ligule.*—Present on adaxial side of leaf at junction of blade and sheath; length: 4 mm; membranaceous, irregular edge.

Leaf blade: Alternate; distichous; sheathing base; parallel veined; narrowly linear, flat, thin.

*Length.*—47–56 cm. Width: 1.5–5.0 cm.

*Entire margin.*—Rose red (Pantone #18-1852), serrulate.

*Midrib.*—White (Pantone #12-5202).

*Adaxial surface.*—Sparsely hirsute.

*Abaxial surface.*—Glabrous except sparsely hirsute along midrib.

*Prominent parallel veins.*—5 per 1 cm width.

INFLORESCENCE

Blooming period: Twice annually in the greenhouse for approximately one month beginning in late April and late October in Tennessee, North Carolina and Mississippi.

Monoecious: Separate male and female flowers on the same plant; variable.

Staminate flowers: May be of two types: one inflorescence type borne as paired spikelets on a slender rachis forming 3–7 racemes arranged in a panicle, the "tassel", at the summit of the culm. Alternatively, staminate spikelets may be borne on a single spike above the pistillate flowers.

*Length.*—6–12 cm.

*Axis.*—Stiff, continuous, ascending.

Spikelet: Two-flowered, one sessile, one pediceled; laterally compressed awnless, attenuate with red (Pantone #19-1860) tip and red (Pantone #19-1860) band at base; Length: 11 mm; Width: 3 mm. In pairs on one side of a persistent central axis.

*Pedicel length.*—3 mm.

*Glumes.*—Outer glume: cartilaginous, tapering to an acute tip, ciliate, flat, several nerved, margins involute, fimbriate. Inner glume: chartaceous.

Pistillate flowers: Borne in leaf axils; spikelets distichously arranged; variable.

*Styles.*—Pilose with distinct bifurcated tips.

*Color.*—Ranges from pastel parchment (Pantone #11-0603) to light lilac (Pantone #12-2903) to rose red (Pantone #18-1852).

*Length.*—100 mm.

One type of pistillate flower consists of a single rowed spike of 4 to 6 triangular caryopses in hard, shell-like fruitcases enclosed in a single leaf sheath; caryopses disarticulate upon maturity. Length: 7.5 mm; Width: 5 mm. Colors range from solid to variegated combinations of the following: White (Pantone #11-0602), gray (Pantone #16-1107), tobacco brown (Pantone #17-1327), brown (Pantone #19-1121), dark brown (Pantone #19-1020). Alternatively, spikelets paired and partially enclosed in stiff, brown speckled glumes; caryopses rounded and imbricate; Spikes enclosed in single or multiple leaf sheaths. Caryopses do not disarticulate upon maturity; Length: 5 mm; Width: 5 mm. Color variegated combinations of the following: dark brown (Pantone #19-1217), brown (Pantone #18-1154), beige (Pantone 15-1225), light beige (Pantone #13-1018).

*Fruit.*—Five to ten ears per culm per blooming period; flowers are produced twice a year under greenhouse conditions; some plants may produce approximately 150 ears twice annually.

*Maturity.*—45 days following fertilization.

A. Ear (husked ear data unless stated otherwise):

*Length.*—About 43 mm.

*Midpoint diameter.*—About 6.7 mm.

*Weight.*—0.5 gm.

*Kernel rows.*—2 (rarely 3–4).

*Silk color (exposed at silking stage).*—light lilac (Pantone #12-2903) to rose red (Pantone #18-1852).

*Husked color.*—Cob kernels are embedded in the rachis segments, some of which disarticulate upon maturity. These segments are brownish gray and are the hard, boney fruitcase enclosing the kernels.

*Kernel color.*—beige (Pantone #14-1122) shading to golden beige (Pantone #16-1336).

*Husked extension (harvest stage).*—About 1 cm.

*Shank.*—About 6.5 cm.

*Taper.*—Slight.

*Position in dry husk stage.*—Upright.

*Drying time (unhusked ear).*—About 2–3 days.

B. Kernel (dried):

*Type I.*—Angular caryopses in hard, shell-like fruitcases, disarticulate upon maturity; Size (from midpoint): Length about 0.8 mm, Width about 0.5 mm, Thickness about 0.4 mm. Shape: Trapezoidal. Colors range from solid to variegated combinations of the following: white (Pantone #11-0602), gray (Pantone #16-1107), tobacco brown (Pantone #17-1327), brown (Pantone #19-1121), dark brown (Pantone #19-1020). Weight 20 seeds (unsized samples): 1.3 gm.

*Type II.*—Paired caryopses partially enclosed in endurated glumes forming a cob, upon maturity do not disarticulate: Size (from midpoint): Length about 3.9 mm, Width about 2.8 mm, Thickness about 2.7 mm. Shape grade (% round): 100% round (tip pointed). Pericarp color: beige (Pantone #14-1122) shading to golden beige (Pantone #16-1336). Aleurone color: Clear. Endosperm color: White (Pantone #11-0601). Endosperm type: Pop. Weight 20 seeds (unsized sapmles): About 0.4 gm.

C. Cob:

*Diameter at midpoint.*—5.3 to 8.7 mm.

*Strength.*—Variable.

*Color.*—Smoke (Pantone #12-0704).

*Alicole.*—Length: About 6.6 mm. External width: 7.0 mm. Internal width: 5.0 mm. External length: 5.5 mm. Internal length: 5.0 mm. Overall length: 6.4 mm. Thickness: About 4.5 mm. Depth: 2.9 mm.

*Cupule.*—Overhang: About 0.6 mm. Left wing width:—1.0 mm. Right wing width: 1.3 mm. Wing height: 4.1 mm. Lower glume length: 5.9 mm. Lower glume angle: About 20°. Lower gllume width: About 3.0 mm. Glume cushion width: 5.4 mm. Glume cushion height: 1.8 mm. Sessile thickness: 0.3 mm. Cupule pubescence: sparse, short hairs. Color: Buff (Pantone #13-1024).

COMPARATIVE PARENTAL CHARACTERISTICS

Leaf blade: *Zea diploperennis* round in cross section; diam. 1 cm. *Tripsacum dactyloides* oval in cross section; diam. 1.3 cm.

Leaf blade: *Z. diploperennis.* Width 1–2 cm; margins pink serrulate from midsection of blade to tip; adaxial surface: sparsely hirsute; prominent veins: 6 per 1 cm width. *T. dactyloides.* Width: 1 cm; margins white serrulate along entire blade; Adaxial surface: hirsute; prominent veins: 12 per 1 cm.

Blooming period: *Z. diploperennis* twice a year in the greenhouse, end of March and end of September for about a month. *T. dactyloides* continuously from May to October.

Stamiante flowers: *Z. diploperennis* borne in tassel at summit of culm. *T. dactyloides* staminate flowers borne above pistillate flowers in single spike.

Pistillate flowers: *Z. diploperennis* caryopsis triangular-trapezoidal in hard bondy fruitcases; Length: 8 mm; Width: 4–5 mm; Color: black (Pantone #19-030), dark brown (Pantone #19-1020) or mottled black-brown. *T. dactyloides* caryopsis trapezoidal in hard, bony fruitcase; Length: 6–10 mm; Width: 6 mm. Color: pale brown (Pantone #17-1137) or buff (Pantone #13-1024).

Color reference: Leatrice Eiseman and Lawrence Herbert, *The Pantone Book of Color.* Harry N. Abrams, Inc., Publishers, New York, 1990.

COMPARISON TO SUN DANCE, U.S. PLANT PAT. NO. 6,906

Although this plant appears quite similar to Sun Dance phenotypically, it is distinct in some traits. It is resistant to aphids and white flies; Sun Dance is not. It has a glossy leaf surface evidenced by a silvery sheen when held under water. Sun Dance does not have such glossy foliage. Tripsacorn is also demonstrated by molecular assay to be distinct from Sun Dance in its nuclear and cytoplasmic DNA as revealed by banding differences to southern blots using nuclear and mitochondrial DNA probes.

I claim:

1. A new and distinct variety of corn plant, substantially as herein shown and described, characterized by its profuse production of fruit, multiple types of inflorescence, bifurcated style, perennial habit, drought tolerance and pest resistance.

* * * * *

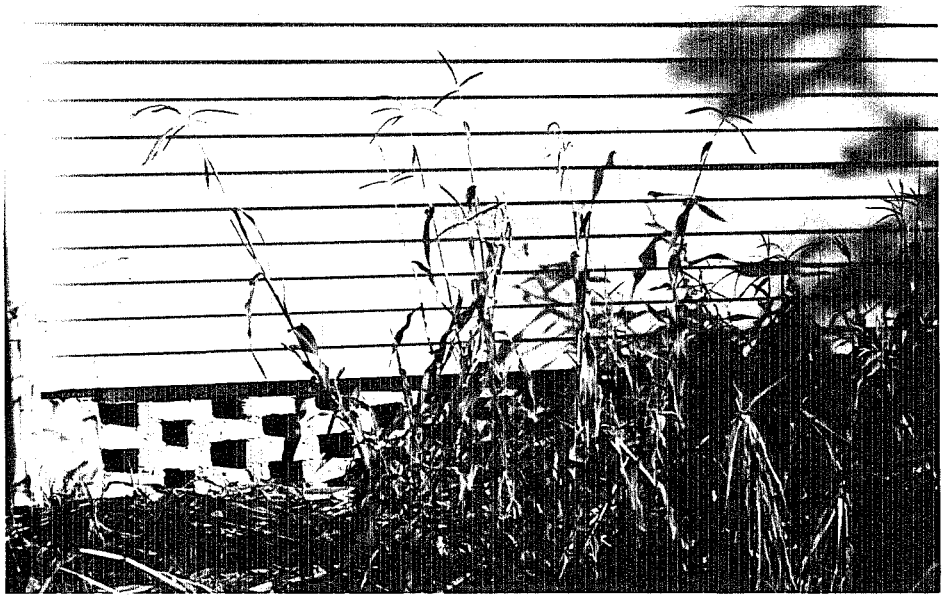
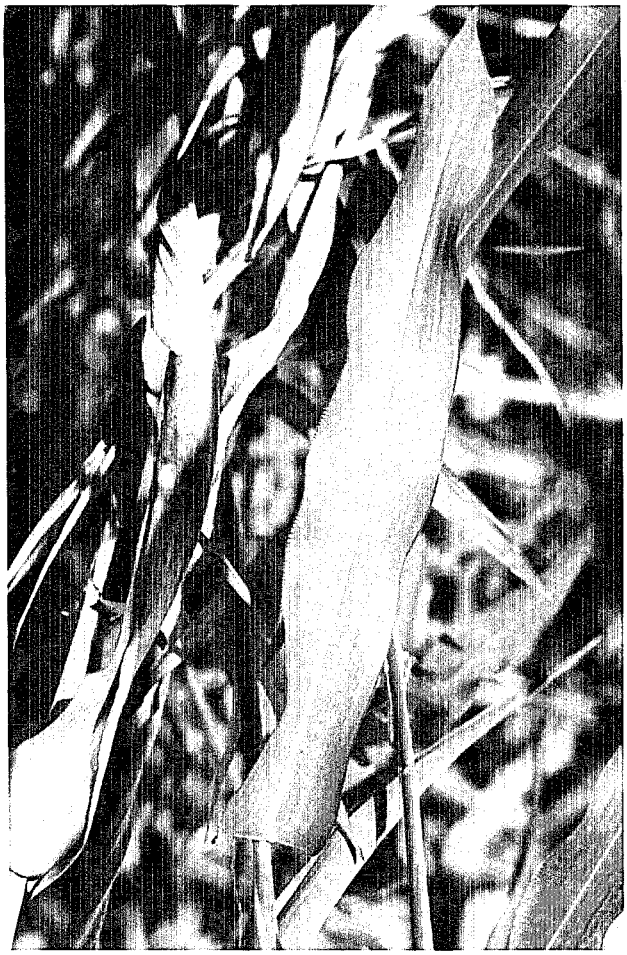

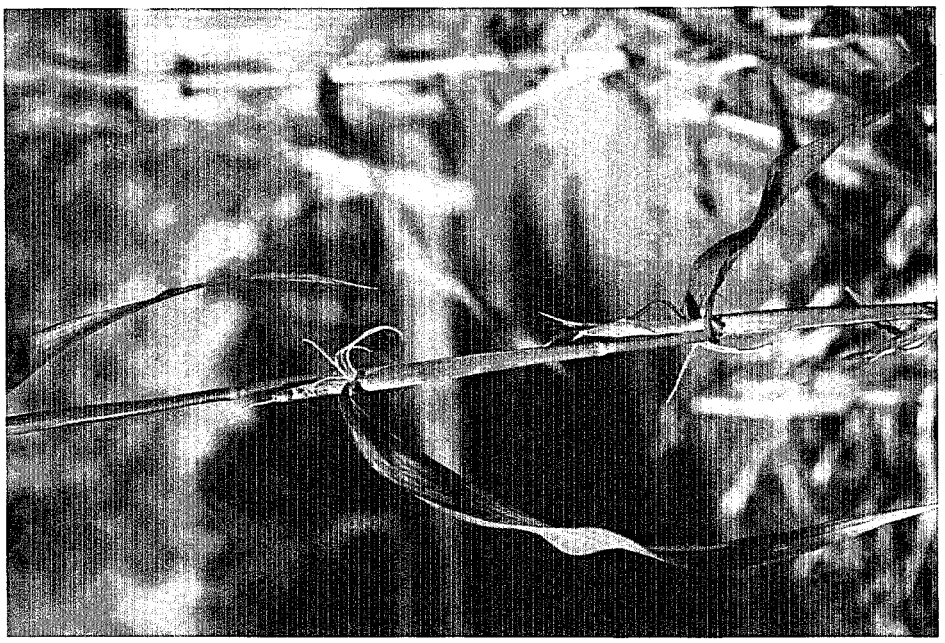
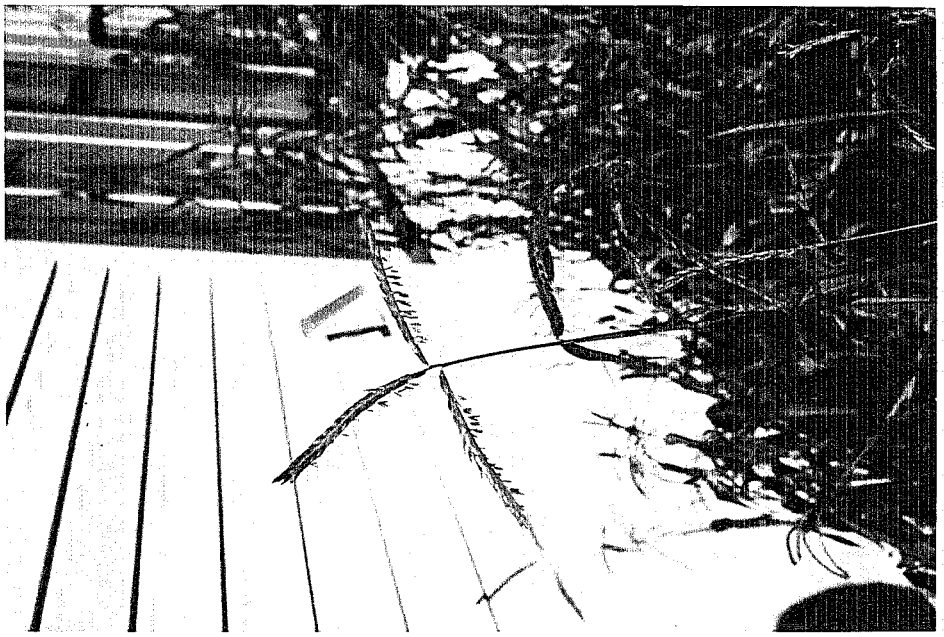

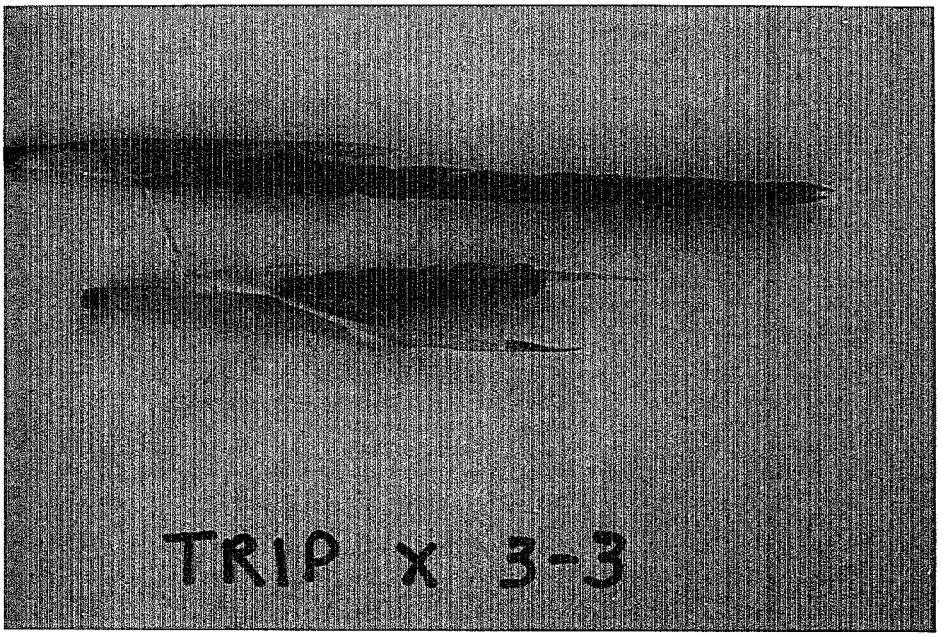
TRIP x 3-3
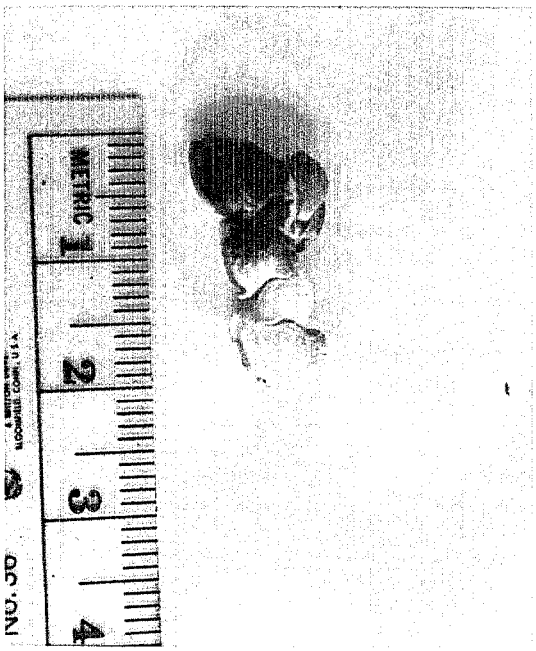
METRIC
1
2
3
4

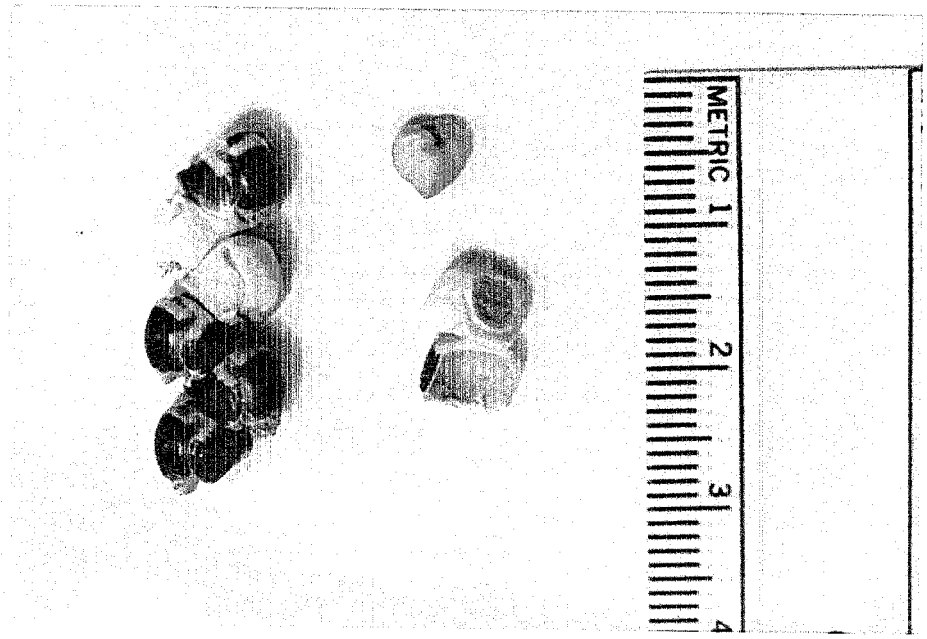
METRIC 1
2
3
4
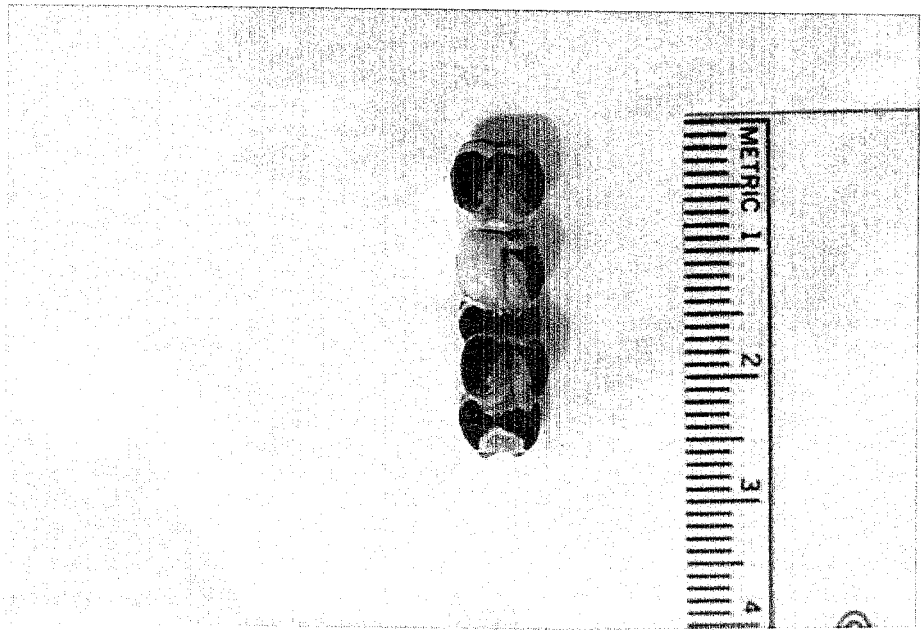
METRIC 1
2
3
4

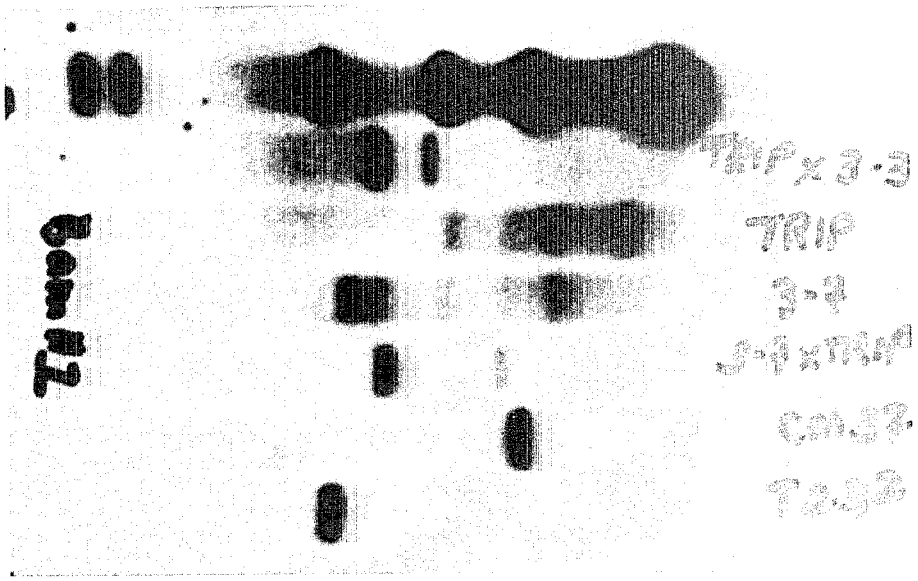
TRIP x 3-3
TRIP
3-7
3-7 x TRIP
Cm37
T282
Band 17
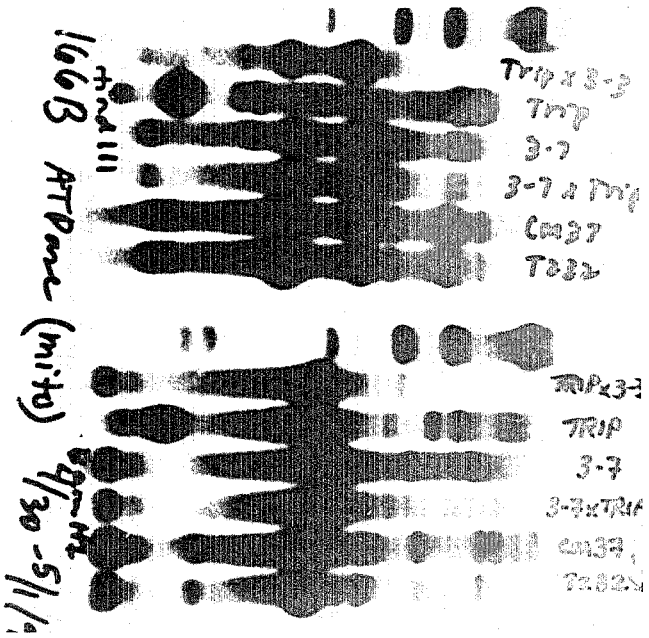
TRIP x 3-3
TRIP
3-7
3-7 x TRIP
Cm37
T282
TRIP x 3-3
TRIP
3-7
3-7 x TRIP
Cm37
T282